United States Patent [19]

Bilstad et al.

[11] 4,341,116

[45] Jul. 27, 1982

[54] LIQUID ABSENCE DETECTOR

[75] Inventors: Arnold C. Bilstad, Deerfield; Michael Wicnienski, Antioch, both of Ill.

[73] Assignee: Baxter Travenol Laboratories, Inc., Deerfield, Ill.

[21] Appl. No.: 127,552

[22] Filed: Mar. 6, 1980

[51] Int. Cl.³ .......................................... G01N 29/02
[52] U.S. Cl. ...................................... 73/290 V; 73/19; 73/632
[58] Field of Search ............... 73/290 V, 19, 599, 620, 73/632; 367/908; 340/621; 310/334, 336

[56] References Cited

U.S. PATENT DOCUMENTS

| | | | |
|---|---|---|---|
| 3,921,622 | 11/1975 | Cole | 73/19 |
| 3,974,681 | 8/1976 | Namery | 73/19 |
| 4,068,521 | 1/1978 | Cosentino et al. | 73/19 |
| 4,121,094 | 10/1978 | DiVito et al. | 367/908 |
| 4,122,713 | 10/1978 | Stasz et al. | 73/19 |
| 4,202,049 | 5/1980 | Wetzel | 73/290 V |

FOREIGN PATENT DOCUMENTS 630191 10/1961 Canada .

*Primary Examiner*—Stephen A. Kreitman
*Attorney, Agent, or Firm*—Paul C. Flattery; Daniel D. Ryan; George H. Gerstman

[57] ABSTRACT

A system is provided for detecting the absence of liquid in a liquid chamber. A signal is transmitted through a liquid chamber and a signal is provided in response to the amplitude of the received signal. A receiving transducer receives an AC signal which is amplified and fed to a DC control circuit. A reference voltage is provided to one input of a comparator and the output of the DC control circuit is fed to the other input of the comparator. The comparator output provides the liquid absence signal if the difference between the reference voltage and the DC control circuit output voltage is less than a predetermined value.

13 Claims, 3 Drawing Figures

LIQUID ABSENCE DETECTOR

BACKGROUND OF THE INVENTION

This invention concerns a novel system for detecting the absence of liquid in a liquid chamber. Such "liquid absence" includes but is not limited to bubbles or liquid level below a predetermined level.

It is often desirable, if not essential, to detect the presence of bubbles in a liquid or the drop in liquid level. For example, in blood processing, such as dialysis, oxygenation, blood fractionation, etc., it is extremely important that the absence of blood resulting from an air leak or any other reason be immediately detected so that the tubing can be clamped before an air bubble is allowed to enter the patient's vein with the blood.

Known in the art are ultrasonic systems for detecting bubbles, in which a signal is transmitted through a liquid chamber containing the liquid and the transmitted signal is received by a receiver after being transmitted through the liquid chamber. The amplitude of the received signal is utilized to determine the presence of bubbles. It is desirable that the system be extremely reliable so that there is minimal chance of error.

To this end, it is an object of the present invention to provide a liquid absence detection system that is very reliable and provides a substantially fail-safe operation.

Another object of the present invention is to provide a liquid absence detection system that is simple in construction and requires a relatively small number of parts.

A further object of the present invention is to provide a liquid absence detection circuit that is efficient to manufacture and easy to repair.

Other objects of the present invention will become apparent as the description proceeds.

SUMMARY OF THE INVENTION

In accordance with the present invention, a system is provided for detecting the absence of liquid in a liquid chamber, in which a signal is transmitted from a transmitter through the liquid chamber containing the liquid and the transmitted signal is received by a receiver after transmission through the liquid chamber.

In the illustrative embodiment, the receiver comprises a receiving transducer for receiving an AC signal, an amplifier, a capacitor AC coupling the transducer to the amplifier, a DC control circuit and means coupling the amplified AC signal to the DC control circuit. A comparator is provided with a reference voltage at one input of the comparator. Means are provided for coupling the DC control circuit output voltage to the other input of the comparator. The DC control circuit output is reflective of the amplitude of the amplified AC signal. The comparator output provides a liquid absence detection signal in response to the difference between the reference voltage and the DC control circuit output voltage.

In the illustrative embodiment, the receiving transducer is connected to a second receiver. The second receiver is energized to operate independently of the first receiver, thereby providing a substantially fail-safe system.

In the illustrative embodiment, the transmitter comprises an oscillator, a plurality of NOR gates connected to operate as an amplifier stage, a pair of push-pull transistors, means coupling the output of the amplifier stages to the input of the push-pull transistors, and a transmitting crystal coupled to the output of the transistors.

A more detailed explanation of the invention is provided in the following description and claims, and is illustrated in the accompanying drawings.

DETAILED DESCRIPTION OF THE ILLUSTRATIVE EMBODIMENT

Figure 1:
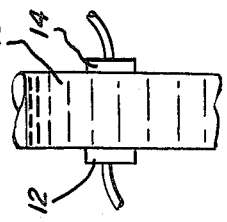
FIG. 1 is a schematic view of a liquid chamber and an attached transmitting crystal and receiving crystals.

Referring to FIG. 1, a liquid chamber 10 is shown therein containing a liquid, with a transmitting crystal 12 attached at one side of the liquid chamber and receiving crystal 14 attached to the opposite side of the liquid chamber. The liquid chamber may be the drip chamber in a blood processing system. An ultrasonic liquid absence detection system is provided in which the signal transmitted from crystal 12 passes through chamber 10 and is received by receiver crystal 14 after transmission through the liquid chamber 10. The amplitude of the received signal decreases significantly if bubbles are present or if the liquid level is down and this liquid absence condition is readily detected.

Figure 2:
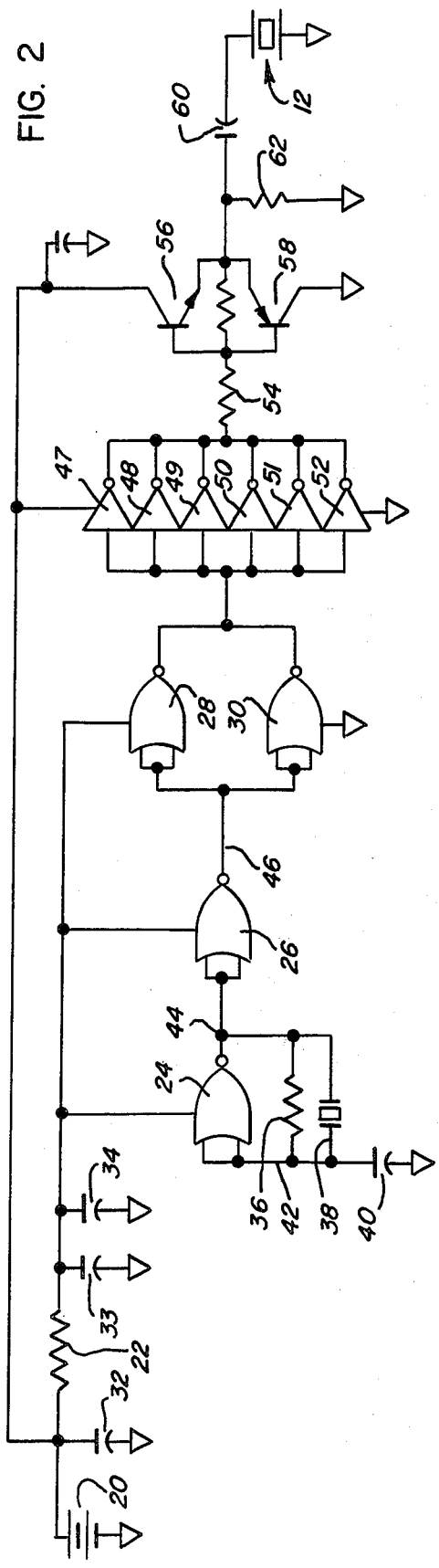
FIG. 2 is a schematic circuit diagram of a transmitter constructed in accordance with the principles of the present invention.
Figure 3:
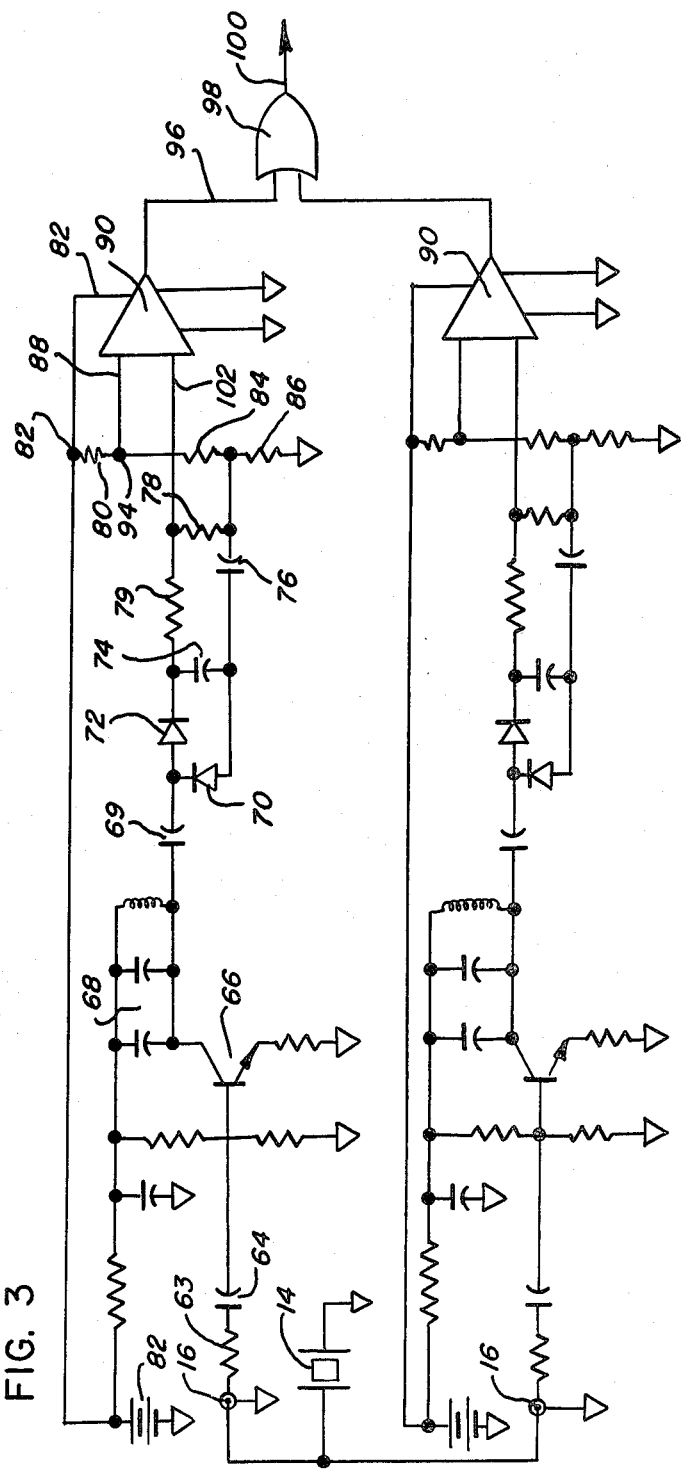
FIG. 3 is a schematic circuit diagram of a pair of receivers constructed in accordance with the principles of the present invention.

The transmitter utilized in connection with the liquid absence detection system of the present invention is illustrated in FIG. 2, and the receivers utilized in connection with the liquid absence detector are illustrated in FIG. 3.

Referring to the transmitter circuit illustrated in FIG. 2, a 15-volt DC source 20 is coupled via current limiting resistor 22 to an integrated circuit package comprising four NOR gates 24, 26, 28 and 30. As a specific example, although no limitation is intended, NOR gate package 14001 may be utilized. A number of filter capacitors 32, 33 and 34 are connected to the line as illustrated.

The NOR gates 24, 26, 28, 30 are not used as NOR gates, but are used instead as amplifiers. An oscillator is formed with NOR gate 24, resistor 36 connected in parallel as illustrated, crystal 38 connected in parallel to resistor 36, and capacitor 40 connected from line 42 to common. The result is a crystal controlled oscillator which preferably oscillates at 2 megahertz. The output 44 of the oscillator is coupled to a further amplification stage which comprises NOR gate 26 and parallely connected NOR gates 28 and 30 connected to the output 46 of NOR gate 26. The amplification by the NOR gates is based on the very high impedance at the input to the gates with a very low impedance at the outputs thereof. By providing the same voltage the power is increased considerably. Thus each NOR gate section comprises an additional stage of amplification.

A further stage of amplification is provided by six paralleled inverters 47, 48, 49, 50, 51 and 52. As a specific example, a single 4049 integrated circuit comprising six inverters is utilized with all of the inputs thereof being connected to the common output of NOR gates 28, 30, and all of the outputs of the inverters 47–52 being connected through resistor 54 to a pair of push-pull transistors 56, 58. The paralleled inverters 47–52 provide an additional stage of amplification. When the signal from the inverters 47–52 is high, transistor 56 is on and transistor 58 is off. Likewise, when the signal through resistor 54 is low, transistor 58 is on and transistor 56 is off. The emitter follower transistors 56, 58 will thus oscillate at the rate of oscillation provided by the previous oscillator stage to drive the transmitting crystal 12 at this frequency (preferably 2 megahertz). Push-pull transistors 56, 58 are coupled to a crystal 12 via AC coupling capacitor 60 and a resistor 62 is a reference to common so that the output from the transistors 56, 58 will not float.

Referring now to FIG. 3, it can be seen that there are two identical receiver circuits each running independently of each other. Thus in the event of a component failure, the system will still be operable. If a certain voltage level is not received by both of the receivers, there will be an indication that a liquid absence condition has been detected.

It is preferred that one of the receiver circuits be the prime receiver while the other receiver circuit be adjusted so that if the prime receiver circuit is inoperable and there is slightly more loss in the fluid path, the secondary receiver will provide a liquid absence detected signal. The receivers are calibrated by the particular resistors associated with the non-inverting inputs of comparators, discussed below, which resistors operate as a voltage divider and by varying the proportions the sensitivity is varied.

Since the construction of the lower receiver is identical to the construction of the upper receiver, the upper receiver will only be described herein. The input transducer, in the form of a receiving crystal 14, is coupled through input jack 16, resistor 63 and capacitor 64 to the base of NPN transistor 66. Resistor 63 is utilized to prevent the two receiver circuits from interacting with each other. Capacitor 64 is an AC coupling capacitor.

The collector of transistor 66 is connected to a tuned filter 68 which is AC coupled through capacitor 69 to a full wave rectifier (comprising diode 70 and diode 72) which is operable to charge capacitor 74 during one half cycle and capacitor 76 during the other half cycle. Thus on the positive half cycle of the input wave, diode 72 will conduct and capacitor 74 will be charged while on the negative half cycle of the input wave, diode 70 will conduct and capacitor 76 will charge. A discharge path is provided through the capacitors and resistors 78 and 79.

A voltage divider is provided by resistor 80 connected to the DC source voltage at point 82, resistor 84 connected to the other side of resistor 80, and resistor 86 connected to the other side of resistor 84, as illustrated. A reference voltage is provided to input 88 of a comparator 90 and the voltage at junction 92 determines the voltage level to which the detected ultrasonic level signal will be added. The voltage at point 94 represents the level that the ultrasonic signal must reach to indicate that proper liquid flow is present. Therefore, if capacitors 74 and 76 are discharged and the voltage level is below the voltage level which must be present at junction 94, the comparator 90 will sense this drop in voltage level and a low output signal will be fed to input 96 of an AND gate 98. A low signal will then be provided on line 100 for further processing such as to effect the clamping of blood tubing and/or sound an alarm.

It can be seen that receiver crystal 14 is AC coupled to an amplifier including transistor 66, and the AC signal is amplified and fed to a DC control circuit. The DC control circuit comprises diodes 70, 72, capacitors 74, 76, resistor 78 and the voltage divider at the output thereof. The non-inverting input 88 of comparator 90 is coupled to a fixed voltage at point 94 while the voltage level at other input 102 of comparator 90 is coupled to the capacitors so that the comparator senses the charge in the capacitors. The voltage level of the capacitors are reflective of the AC voltage level. As the reception increases, the AC voltage level increases and the capacitor voltage level increases. The comparator compares the DC voltage on the capacitors with the fixed voltage at point 94 and if the difference is greater than a predetermined amount, the reception is considered satisfactory. However, if the difference is less than the predetermined amount, that indicates that there is a reception problem thus indicating the possibility of liquid absence. Anything which causes the difference of the voltages at inputs 88 and 102 to be less than the predetermined amount will operate to provide a low signal to one of the inputs of AND gate 98, thereby providing a low signal at the output 100 of AND gate 98.

In a preferred embodiment, capacitors 74, 76 and resistors 78, 79 are chosen to provide a fast charge time and a slow discharge time. This will enable the system to ignore very small or individual bubbles and will enable the system primarily to detect the liquid level in a drip chamber. However, modifications regarding the charge and discharge times may be made to accomodate the appropriate sensitivity required.

The lower receiver circuit in FIG. 3 operates in the same manner as described above with respect to the upper receiver circuit. Thus during normal operation a high signal is provided to both inputs of AND gate 98 and if either comparator 90 or comparator 90' senses a difference between the reference voltage and the DC voltage on the capacitor that is less than the predetermined amount, a low signal will be provided on output 100 to cause an alarm and/or to clamp the blood tubing and/or to provide other processing as a result of detected liquid absence or a failure problem.

Although an illustrative embodiment of the invention has been shown and described, it is to be understood that various modifications and substitutions may be made by those skilled in the art without departing from the novel spirit and scope of the present invention.

What is claimed is:

1. A device for detecting the absence of liquid in a liquid chamber, said device comprising
   transmitter means for transmitting a signal through the chamber, and
   receiver means for receiving the transmitted signal after its transmission through the chamber, said receiver means comprising
   a receiving transducer for receiving an AC signal,
   an amplifier,
   a capacitor AC coupling said transducer to said amplifier,
   DC control circuit means for receiving an AC signal and for generating an output voltage the amplitude of which is proportional to the peak-to-peak amplitude of the received AC signal,
   means for coupling the amplified AC signal from said amplifier to said DC control circuit means,
   a comparator,
   means for providing a reference voltage to one input of said comparator,
   means for coupling said DC control circuit output voltage to the other input of said comparator, the amplitude of said DC control circuit output voltage being proportional of the peak to peak amplitude of said amplified AC signal, and said comparator output providing a liquid absence detection signal in response to the difference between said reference voltage and said DC control circuit output voltage.

2. A device according to claim 1, wherein said DC control circuit means comprises a capacitor charging circuit having a first capacitor which is charged to a voltage that is proportional to the positive half-cycle amplitude of said amplified AC signal and a second capacitor which is charged to a voltage that is proportional to the negative half-cycle amplitude of said amplified AC signal, said DC control circuit output voltage comprising the combined charge of each of said capacitors.

3. A device according to claim 1 or 2, wherein said comparator is operative to signal the absence of liquid if the difference between said reference voltage and said DC control circuit output voltage is less than a predetermined value.

4. A device according to claim 1 or 2, and further including second receiver means substantially identical to said first-mentioned receiver means, and means coupling said receiving transducer to said second receiver means, for operation of said second receiver means independently of said first receiver means.

5. A device according to claim 1 or 2, wherein said transmitter means comprises an oscillator, a plurality of NOR gates connected to operate as an amplifier stage, a pair of push-pull transistors, means coupling the output of said amplifier stage to the input of said push-pull transistors, and a transmitting crystal coupled to the output of said transistors.

6. A device according to claim 5, wherein said transmitter means includes a plurality of inverters coupled in parallel and connected intermediate said NOR gates and said push-pull transistors.

7. A device for detecting the absence of liquid in a liquid chamber, said device comprising transmitter means for transmitting a signal through the chamber said transmitter means comprising an oscillator, a plurality of NOR gates connected to operate as an amplifier stage, a pair of push-pull transistors, means coupling the output of said amplifier stage to the input of said push-pull transistors, and a transmitting crystal coupled to the output of said transistors, and receiver means for receiving the transmitted signal after its transmission through the chamber.

8. A device according to claim 7, wherein said transmitter means includes a plurality of inverters coupled in parallel and connected intermediate said NOR gates and said push-pull transistors.

9. A device according to claim 7 or 8 wherein said receiver means includes a receiving transducer for receiving an AC signal, an amplifier, a capacitor AC coupling said transducer to said amplifier, DC control circuit means for receiving an AC signal and for generating an output voltage which is reflective of the amplitude of the received AC signal, means for coupling the amplified AC signal from said amplifier to said DC control circuit, a comparator, means providing a reference voltage to one input of said comparator, means for coupling the DC control circuit output voltage to the other input of the comparator, the amplitude of said DC control circuit output voltage being reflective of the amplitude of the amplified AC signal, and said comparator output providing a liquid absence detection signal in response to the difference between said reference voltage and said DC control circuit output voltage.

10. A device according to claim 9 wherein said DC control circuit means includes means for receiving said amplified AC signal and for generating said DC control circuit output voltage the amplitude of which is proportional to the peak-to-peak amplitude of said amplified AC signal.

11. A device according to claim 9 wherein said DC control circuit means includes a capacitor charging circuit having a first capacitor which is charged to a voltage that is proportional to the positive half-cycle amplitude of said amplified AC signal and a second capacitor which is charged to a voltage that is proportional to the negative half-cycle amplitude of the amplified AC signal, said DC control circuit output voltage comprising the combined charge of each of said capacitors.

12. A device according to claim 9 and further including second receiver means substantially identical to said first-mentioned receiver means, and means coupling said receiving transducer to said second receiver means for operation of said second receiver means independently of said first receiver means.

13. A device according to claim 9 wherein said comparator is operative to signal the absence of liquid if the difference between said reference voltage and said DC control circuit output voltage is less than a predetermined value.

* * * * *